United States Patent
Angibaud (10) Patent No.: US 8,287,600 B2
(45) Date of Patent: Oct. 16, 2012

(54) MOUNTING SYSTEM AND METHOD FOR ENHANCING IMPLANT FIXATION TO BONE

(75) Inventor: Laurent Angibaud, Gainesville, FL (US)

(73) Assignee: Exactech, Inc., Gainesville, FL (US)

( * ) Notice: Subject to any disclaimer, the term of this patent is extended or adjusted under 35 U.S.C. 154(b) by 1423 days.

(21) Appl. No.: 11/557,416

(22) Filed: Nov. 7, 2006

(65) Prior Publication Data

US 2007/0150065 A1    Jun. 28, 2007

Related U.S. Application Data

(60) Provisional application No. 60/734,181, filed on Nov. 7, 2005.

(51) Int. Cl.
*A61F 2/38* (2006.01)
(52) U.S. Cl. ............... 623/20.32; 623/20.15; 623/20.34
(58) Field of Classification Search ............... 623/20.14, 623/20.34, 20.15, 20.25, 20.32, 23.44
See application file for complete search history.

(56) References Cited

U.S. PATENT DOCUMENTS

| | | |
|---|---|---|
| 3,869,730 A | 3/1975 | Skobel |
| 3,978,528 A | 9/1976 | Crep |
| 4,003,095 A | 1/1977 | Gristina |
| 4,040,131 A | 8/1977 | Gristina |
| 4,179,758 A | 12/1979 | Gristina |
| 4,206,517 A | 6/1980 | Pappas |
| 4,229,840 A | 10/1980 | Gristina |
| 4,261,062 A | 4/1981 | Amstutz et al. |
| 4,550,450 A | 11/1985 | Kinnett |
| 4,653,487 A | 3/1987 | Maale |
| 4,693,723 A | 9/1987 | Gabard |
| 4,822,366 A | 4/1989 | Bolesky |
| 4,959,071 A | 9/1990 | Brown et al. |
| 4,964,865 A | 10/1990 | Burkhead et al. |
| 4,986,833 A | 1/1991 | Worland |
| 5,013,313 A | 5/1991 | Surer |
| 5,032,132 A | 7/1991 | Matsen, III et al. |
| 5,080,673 A | 1/1992 | Burkhead et al. |
| 5,154,719 A | 10/1992 | Cotrel |
| 5,255,838 A | 10/1993 | Gladdish, Jr. et al. |
| 5,413,605 A * | 5/1995 | Ashby et al. ............... 623/20.34 |
| 5,437,677 A | 8/1995 | Shearer et al. |

(Continued)

FOREIGN PATENT DOCUMENTS

EP    0345 133    6/1989

(Continued)

OTHER PUBLICATIONS

"MaioR Biojoint System", FINCERAMICA (4 pages), 2007.

(Continued)

*Primary Examiner* — David H Willse
*Assistant Examiner* — Javier Blanco
(74) *Attorney, Agent, or Firm* — Greenberg Traurig, LLP (57) ABSTRACT

The present invention relates to a mounting system and method for enhancing implant fixation to bone. That is, the present invention relates generally to the field of orthopaedics. Various embodiments of the present invention relate to the replacement (totally or partially) of a joint. In one example (which example is intended to be illustrative and not restrictive), the present invention provides a modular system with different anchoring mechanisms for optimized fixation of a joint implant to the bone (wherein "optimized" fixation may be as desired by a surgeon).

26 Claims, 9 Drawing Sheets

U.S. PATENT DOCUMENTS

| | | | |
|---|---|---|---|
| 5,462,563 | A | 10/1995 | Shearer et al. |
| 5,489,310 | A | 2/1996 | Mikhail |
| 5,593,448 | A | 1/1997 | Dong |
| 5,611,800 | A | 3/1997 | Davis et al. |
| 5,702,447 | A | 12/1997 | Walch et al. |
| 5,702,453 | A | 12/1997 | Rabbe et al. |
| 5,755,800 | A | 5/1998 | O'Neil et al. |
| 5,800,551 | A | 9/1998 | Williamson et al. |
| 5,976,141 | A | 11/1999 | Haag et al. |
| 5,989,254 | A | 11/1999 | Katz |
| 6,156,069 | A | 12/2000 | Amstutz |
| 6,228,119 | B1 | 5/2001 | Ondrla et al. |
| 6,228,120 | B1 | 5/2001 | Leonard |
| 6,364,910 | B1 | 4/2002 | Shultz et al. |
| 6,379,386 | B1 | 4/2002 | Resch et al. |
| 6,406,495 | B1 | 6/2002 | Schoch |
| 6,514,287 | B2 | 2/2003 | Ondrla et al. |
| 6,673,115 | B2 | 1/2004 | Resch et al. |
| 6,679,916 | B1 | 1/2004 | Frankle et al. |
| 6,699,289 | B2 | 3/2004 | Iannotti et al. |
| 6,736,851 | B2 | 5/2004 | Maroney |
| 6,790,234 | B1 | 9/2004 | Frankle |
| 6,911,047 | B2 | 6/2005 | Rockwood, Jr. et al. |
| 2002/0120340 | A1* | 8/2002 | Metzger et al. ............ 623/20.15 |
| 2003/0028196 | A1 | 2/2003 | Bonutti |
| 2003/0158606 | A1* | 8/2003 | Coon et al. ................. 623/20.15 |
| 2004/0006342 | A1 | 1/2004 | Altarac et al. |
| 2004/0059424 | A1 | 3/2004 | Guederian et al. |
| 2004/0064190 | A1 | 4/2004 | Ball et al. |
| 2004/0122519 | A1 | 6/2004 | Wiley et al. |
| 2004/0122520 | A1 | 6/2004 | Lipman et al. |
| 2004/0225360 | A1 | 11/2004 | Malone |
| 2005/0015131 | A1 | 1/2005 | Fourcault et al. |
| 2005/0015153 | A1* | 1/2005 | Goble et al. ................ 623/23.46 |
| 2005/0049709 | A1 | 3/2005 | Tornier |
| 2005/0060039 | A1 | 3/2005 | Cyprien |
| 2005/0209700 | A1 | 9/2005 | Rockwood, Jr. et al. |

FOREIGN PATENT DOCUMENTS

| | | |
|---|---|---|
| EP | 0 538 895 | 4/1993 |
| EP | 0 552 950 A1 | 7/1993 |
| EP | 0 884 032 A1 | 12/1998 |
| EP | 0 998 885 | 5/2000 |
| EP | 1 486 183 | 12/2004 |
| EP | 1486 183 | 12/2004 |
| EP | 152 0561 | 4/2005 |
| FR | 277 6506 | 10/1999 |
| FR | 279 0 198 | 1/2000 |
| WO | 00/06056 A1 | 2/2000 |

OTHER PUBLICATIONS

Supplementary Partial European Search Report issued in European Patent Appln. No. 06851320.9 dated Mar. 15, 2012.

* cited by examiner

MOUNTING SYSTEM AND METHOD FOR ENHANCING IMPLANT FIXATION TO BONE

RELATED APPLICATIONS

This application claims the benefit of U.S. Provisional Application Ser. No. 60/734,181, filed Nov. 7, 2005, which is incorporated herein by reference in its entirety.

FIELD OF THE INVENTION

The present invention relates to a mounting system and method for enhancing implant fixation to bone. That is, the present invention relates generally to the field of orthopaedics.

Various embodiments of the present invention relate to the replacement (totally or partially) of a joint.

In one example (which example is intended to be illustrative and not restrictive), the present invention provides a modular system with different anchoring mechanisms for optimized fixation of a joint implant to the bone (wherein "optimized" fixation may be as desired by a surgeon).

As used herein, the terms "medial," "medially," and the like mean pertaining to the middle, in or toward the middle, and/or near the middle of the body when standing upright. Conversely, the terms "lateral," "laterally," and the like are used herein as opposed to medial. For example, the medial side of the knee is the side closest to the other knee and the closest sides of the knees are medially facing, whereas the lateral side of the knee is the outside of the knee and is laterally facing.

Further, as used herein, the terms "superior" and "superiorly" mean closer to the top of the head and/or farther from the bottom of the feet when standing upright. Conversely, the term "inferior" and "inferiorly" is used herein as opposed to superior. For example, the heart is superior to the stomach, whereas the stomach is inferior to the heart.

Additionally, as used herein, the terms "anterior," "anteriorly," and the like mean nearer to the front or facing away from the front of the body when standing upright, as opposed to "posterior," "posteriorly," and the like, which mean closer to the back or facing away from the back of the body.

BACKGROUND OF THE INVENTION

Total joint arthroplasty is the surgical replacement of a joint with a prosthesis. A typical knee prosthesis has three main components: a femoral implant, a tibial implant, and a tibio-femoral insert. In general, the femoral component is designed to replace the distal femoral condyles and is typically made from metal. It typically includes rounded surfaces to emulate the condyles, and an elongated stem or pegs for anchoring to the distal femur. In general, the tibial implant is designed to support and align the tibio-femoral insert. The tibial component is also typically made from metal. It typically includes a substantially planar plate portion for supporting the insert and an elongated stem for anchoring to the proximal tibia. In general, the tibio-femoral insert is designed to replace the tibial plateau and the meniscus of the knee. It is typically somewhat disk-shaped and typically includes one or more substantially planar surfaces that bear on the top of the tibial implant and one or more generally concave surfaces that bear against the rounded surfaces of the femoral implant. The insert is generally made of a strong, smooth and low wearing plastic.

Among those benefits and improvements that have been disclosed, other objects and advantages of this invention will become apparent from the following description taken in conjunction with the accompanying figures. The figures constitute a part of this specification and include illustrative embodiments of the present invention and illustrate various objects and features thereof.

DETAILED DESCRIPTION OF THE INVENTION

Detailed embodiments of the present invention are disclosed herein; however, it is to be understood that the disclosed embodiments are merely illustrative of the invention that may be embodied in various forms. In addition, each of the examples given in connection with the various embodiments of the invention are intended to be illustrative, and not restrictive. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

One embodiment of the present invention provides a modular system with different anchoring mechanisms for optimized fixation of an implant with the bone (wherein "optimized" fixation may be as desired by a surgeon). By way of example, and not limitation, the present invention can be applied to the anchorage of an implant for the knee joint, ankle joint, hip joint, shoulder joint, elbow joint, wrist joint, or other joints. Set forth below are several embodiments of the present invention used in association with preparing and anchoring an implant to the proximal end of the patient's resected tibia. It is again noted that these embodiments are only given by way of example, and one skilled in the art based on the teaching provided herein would be able to use corresponding implants and methods to prepare and/or mount and/or anchor an implant to other articulating joint surfaces.

When applied to the knee joint and, more particularly, the tibial implant, the present invention may include at least a tibial plate, a tibial stem, and a locking component. The stem may include several portions associated with different textures. For example (which example is intended to be illustrative and not restrictive), the proximal portion of the stem may be cylindrical and may define the first portion. The second portion may be threaded and may be located below the first portion (considering the stem is placed in the tibia of a patient in a standing position). Optionally, a distal stem could be considered as a third portion. The stem may be defined by a socket or recess having a circular and generally cylindrically-shaped portion opening from the proximal top. While the axis of the recess could be parallel to the axis of the first portion, the axes are not necessarily colinear. The tibial plate may include a generally cylindrically-shaped protuberance extending from its distal surface. The tibial plate and the protuberance may define a through-channel. Generally, the protuberance could fit inside the tibial stem recess. A component may be used to lock the position of the tibial plate relative to the tibial stem.

In one embodiment, the present invention defines a method where the tibial stem is placed first inside the cavity prepared in the proximal tibia. The tibial stem could be anchored to the tibia using several options well known to those skilled in the art (e.g. press-fit, cemented, etc.). The tibial plate is then placed against the proximal resected tibia. Finally, a locking feature locks the orientation of the tibial plate relative to the tibial stem in a desired orientation relative to the resected proximal tibia.

Depending on the design of the connection between the tibial plate and the tibial stem (many examples of which are described herein), the degree of freedom could be adjusted one to six degrees or more. In other words, when the surgeon places the tibial stem inside the cavity prepared in the proximal tibia, it is still possible to adjust the location and orientation of the tibial plate in order to cover the resected tibia.

Notably, an axial load may be applied to the tibial plate against the proximal resected tibia. In cases where the tibial plate is cemented to the proximal resected tibia, the axial load may pressurize the cement mantle during its curing stage (which pressurization may be vital to the long-term fixation of the tibial component).

In one example (which example is intended to be illustrative and not restrictive), the distance from the distal tip of the tibial plate protuberance to the inferior surface of the tibial plate may be less than about 20 or 25 mm. Such size could permit the surgeon to implant the tibial apparatus using a minimally-invasive incision (because minimally-invasive surgery reduces the size of the surgical site, it also reduces the amount of space available for inserting, aligning and securing conventional tibial components such as those associated with conventional stems longer than about 25 mm).

Figure 1:
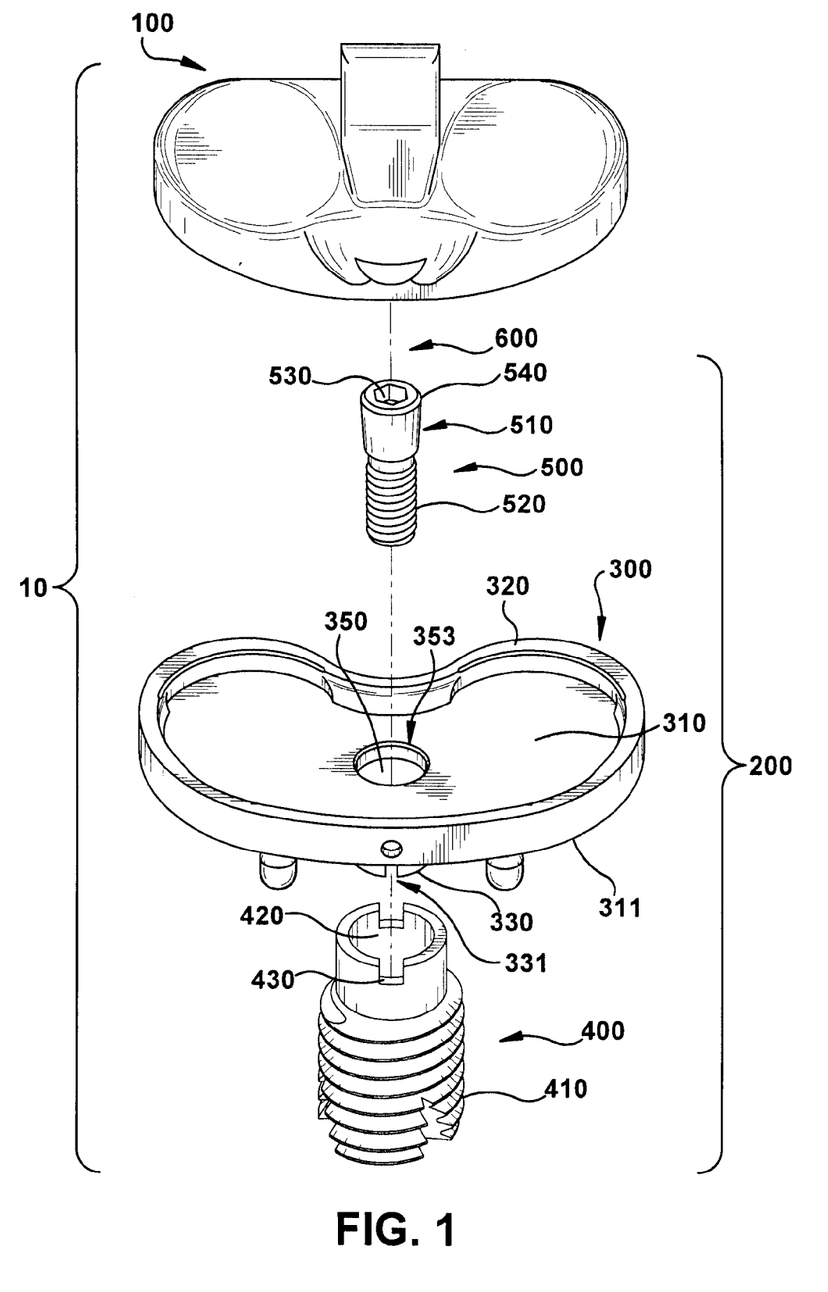
FIG. 1 shows a partially exploded perspective view of an apparatus according to an embodiment of the present invention.
Figure 2:
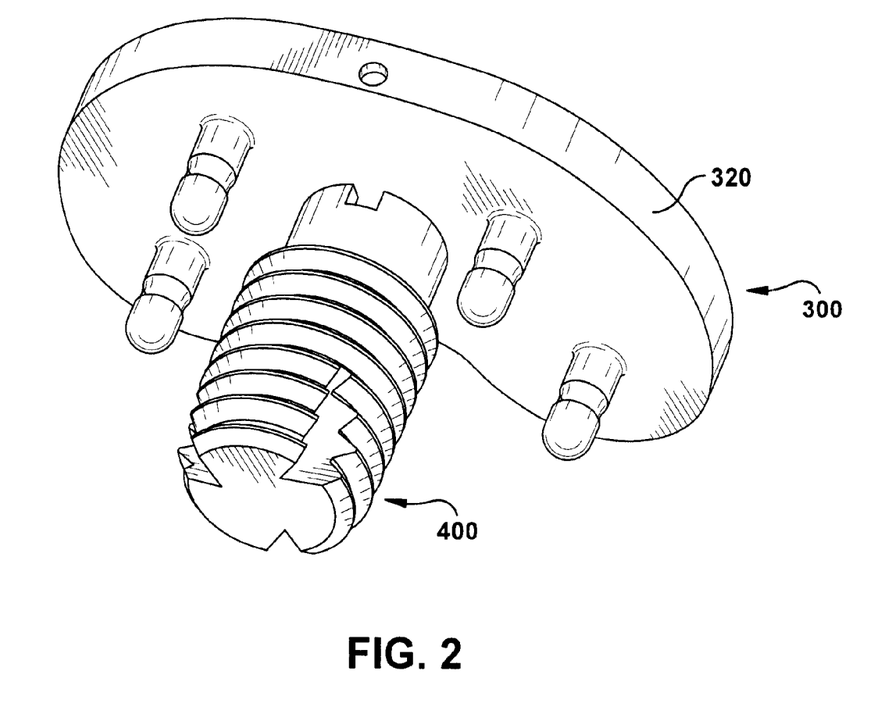
FIG. 2 shows a bottom view a component of FIG. 1.
Figure 3:
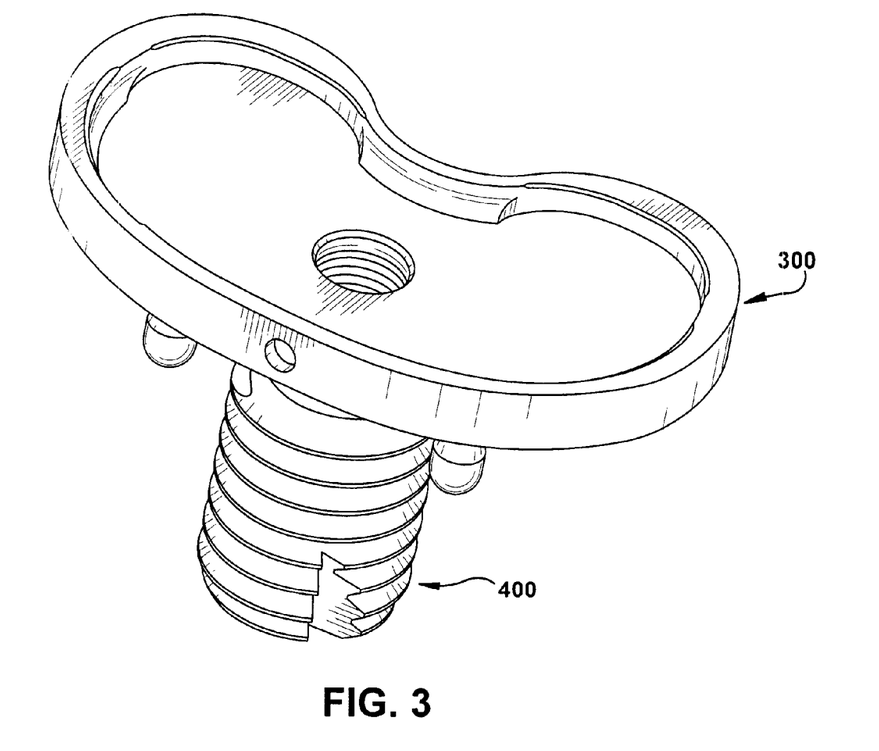
FIG. 3 shows an upper view of a component of FIG. 1.

Referring now to the figures, FIG. 1 shows a partially exploded perspective view of Apparatus 10 according to a first embodiment of the present invention. As seen in this Figure, Apparatus 10 includes Tibio-Femoral Bearing Insert 100. Tibio-Femoral Bearing Insert 100 includes a pair of smooth surfaces configured to serve as bearing surfaces against a pair of femoral codyles (not shown). In one example (which example is intended to be illustrative and not restrictive), Tibio-Femoral Bearing Insert 100 may be made from Ultra High Molecular Weight Polyethylene ("UHMWPE"). In another example (which example is intended to be illustrative and not restrictive), Tibio-Femoral Bearing Insert 100 may be manufactured by Direct Compression Molding ("DCM"). Of course, if desired, Tibio-Femoral Bearing Insert 100 may be made from any suitably strong, smooth, and low-wearing biocompatible material(s).

Figure 4:
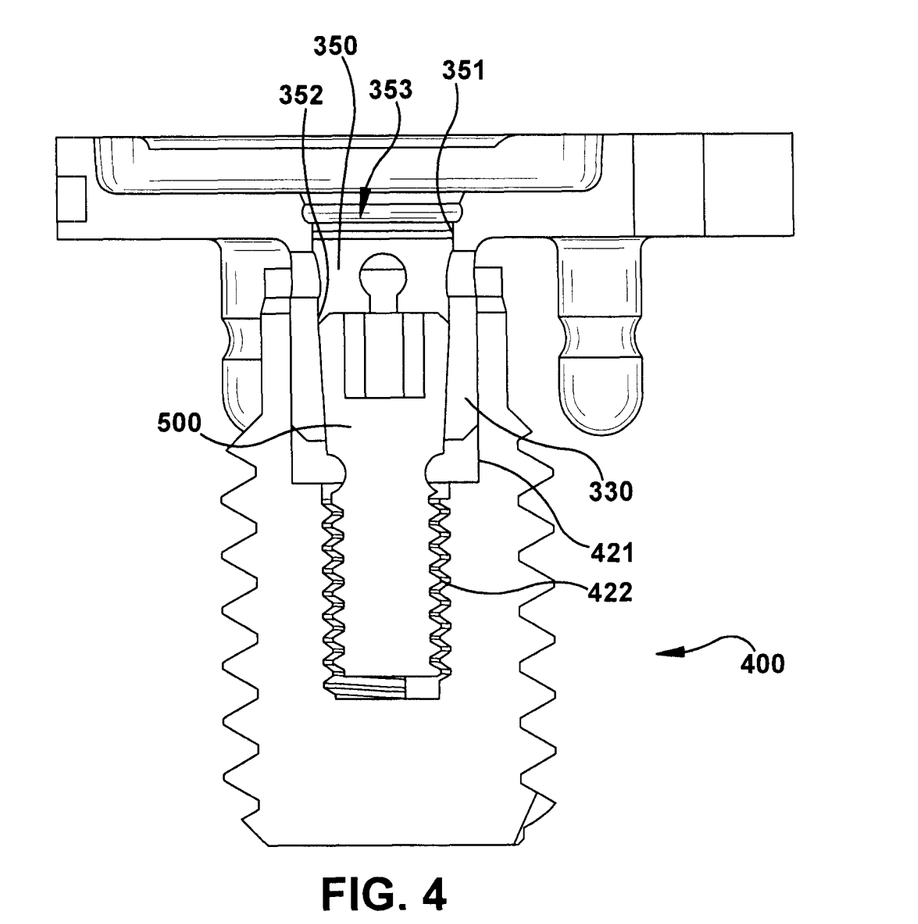
FIG. 4 shows a cross section of various components of FIG. 1 (along a plane including a strict anterior-posterior axis and the vertical axis 600 defined FIG. 1)

Apparatus 10 further includes Tibial Implant 200, which, among other things, is configured to support Tibio-Femoral Bearing Insert 100. In one example (which example is intended to be illustrative and not restrictive), Tibial Implant 200 may be made from a titanium alloy. Of course, if desired, Tibial Implant 200 may be made from a cobalt chrome alloy or any other suitable biocompatible material(s). In any any case, Tibial Implant 200 includes Tibial Plate 300. Among others things, the Superior Surface 310 of Tibial Plate 300 is configured to support the Tibio-Femoral Bearing Insert 100. Tibial Plate 300 further includes a Retaining Wall 320 substantially bounding and extending generally perpendicularly away from Superior Surface 310. It should be appreciated that Retaining Wall 320 is intended for the alignment and the retention of Tibio-Femoral Bearing Insert 100 with Tibial Plate 300. Extending from Inferior Surface 311 of the Tibial Plate 300 is a Protuberance 330 (see, e.g., FIG. 4). In one example (which example is intended to be illustrative and not restrictive), the inferior to superior length of Protuberance 330 may be less than 25 mm (measured from the distal tip of Protuberance 330 to the Inferior Surface 311 of Tibial Plate 300, perpendicularly to Inferior Surface 311). In another example (which example is intended to be illustrative and not restrictive), Protuberance 330 may include at least one Groove 331. Tibial Plate 300 and Protuberance 330 define a Passageway (or through-channel) 350 (see, e.g., FIG. 4) axially extending all the way through Superior Surface 310, Inferior Surface 311 and Protuberance 330 along Axis 600 (see, e.g., FIG. 1). Passageway 350 includes a generally cylindrical shape in its superior portion (First Portion 351) and a tapered portion inferiorly (Second Portion 352) at the level of Protuberance 330. First Portion 351 of Passageway 350 may include Groove 353 intended to fully secure the Tibio-Femoral Bearing Insert 100 with the Tibial Plate 300.

Tibial Implant 200 further includes Tibial Stem 400. Among other things, Tibial Stem 400 is configured as a peg or cage-like structure to be solidly anchored in a cavity created in the proximal tibia. The external shape of Tibial Stem 400 may be generally cylindrical. According to one embodiment, Portion 410 of the cylinder may be threaded in order to screw Tibial Stem 400 in the cavity of the proximal tibia. Toward this end, the superior portion may provide some feature(s), represented here by Groove 430, for the attachment of a screwdriver or other driving device (not shown). Further, Tibial Stem 400 defines Socket 420 having generally a cylindrical First Portion 421 intended to receive and fit with Protuberance 330 of Tibial Plate 300 and Second Portion 422 threaded to receive Locking Component 500.

Referring now once again to Tibial Implant 200, it is seen that this Locking Component 500 may be included. Among other things, Locking Component 500 includes a Tapered Portion 510 intended to fit with Second Portion 352 (i.e., the tapered portion) of Passageway 350 of Tibial Plate 300. Similarly, Locking Component 500 includes Threaded Portion 520 intended to be screwed into the internally threaded Second Portion 422 of Tibial Stem 400. In one example (which example is intended to be illustrative and not restrictive), Locking Component 500 defines a socket 530 having a noncircular shaped opening from its Head 540. By screwing Locking Component 500 relative to Tibial Plate 300 and Tibial Stem 400, the axial translation of Locking Component 500 will generate by its Tapered Portion 510 an enlargement of the protuberance 330 (via Groove 331), and then a locking of Tibial Plate 300 relative to Tibial Stem 400 by friction.

According to another embodiment, the external shape of the tibial stem could be any shape with any texture susceptible to providing an appropriate anchorage in a cavity in the proximal tibia.

Figure 5:
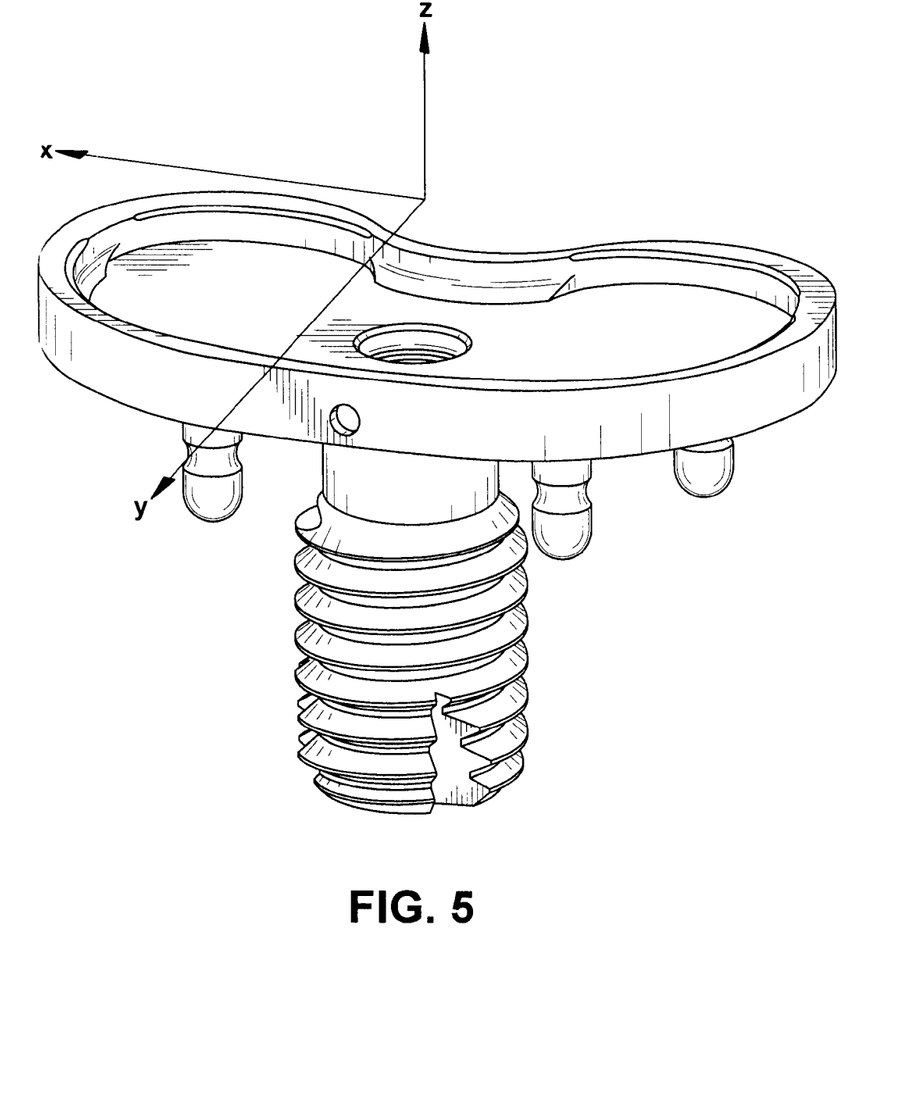
FIG. 5 shows an X, Y and Z coordinate system used in describing certain aspects of the present invention.

Referring now to FIG. 5, it is seen that this Fig. describes a coordinate system, where axis Z is a vertical axis (which could be considered parallel to the intramedullary axis of the tibia if the tibia shows no posterior slope). Further, Axis Y represents the medial-lateral axis, while axis X represents the anterior-posterior axis.

In this regard, according to the first embodiment, Protuberance 330 could be cylindrical. Such a design would allow a potential adjustment to the orientation of Tibial Plate 300 of two degrees of freedom after insertion of cylindrical Protuberance 330 inside Socket 420 of Tibial Stem 400. These two degrees of freedom are translation along Z and rotation around Z and are characteristic of a cylinder-in-cylinder joint.

According to another embodiment, Protuberance 330 could include a spherical portion (for which the diameter is slightly undersized relative to the diameter of Socket 420 of Tibial Stem 400). Such a design would allow a potential adjustment of Tibial Plate 300 orientation according to four degrees of freedom after insertion of the spherical Protuberance 330 inside the Socket 420 of the Tibial Stem 400. These four degrees of freedom are translation along Z, rotation around X, rotation around Y, and rotation around Z and are characteristic of a ball-in-cylinder joint.

According to another embodiment, compatible (for example) with the first and second embodiments, the axis of revolution of Socket 420 may be collinear with the axis of revolution of the external shape of Tibial Stem 400 (where the external shape could provide an additional axis of revolution).

According to another embodiment, compatible (for example) with the first and second embodiments, the axis of revolution of Socket 420 may be parallel but not collinear with the axis of revolution of the external shape of Tibial Stem 400 (where the external shape provides an additional axis of revolution). The offset between these two axes could be helpful, for example, in the case where the intramedullary canal of the tibia is offset. In one example (which example is intended to be illustrative and not restrictive), the offset between these two axes could be between 1 mm and 10 mm. In a more specific example (which example is intended to be illustrative and not restrictive), the offset between these two axes could be about 5 mm. In such offset cases, the surgeon typically uses what is called a tibial tray with an offset tibial stem. In this embodiment, the rotation of Tibial Stem 400 around the axis of revolution of its external shape will provide an adjustment of the axis of revolution position of Socket 420 of Tibial Stem 400 and, as a consequence, allow a potential adjustment of Tibial Plate 300 orientation according to two degrees of freedom after insertion of Protuberance 330 inside Socket 420 of Tibial Stem 400. These two degrees of freedom are translation along X and translation along Y.

According to another embodiment, compatible (for example) with the first embodiment, the axis of revolution of Socket 420 is not parallel with the axis of revolution of the external shape of Tibial Stem 400. In this embodiment, the rotation of Tibial Stem 400 around the axis of revolution of its external shape will provide an adjustment of the position of the axis of revolution of Socket 420 of Tibial Stem 400 and, as a consequence, allow a potential adjustment to the orientation of Tibial Plate 300 according to one degree of freedom after insertion of Protuberance 330 inside Socket 420 of Tibial Stem 400. The one-degree of freedom is a rotational degree of freedom.

With the description of the present invention contained herein, it should be well understood that, regarding (a) the joint type design between Protuberance 330 of Tibial Plate 300 and Socket 420 of Tibial Stem 400 and (b) the orientation of the axis of revolution of Socket 420 relative to the axis of revolution of the external shape of Tibial Stem, Tibial Plate 300 could be adjusted from one degree of freedom to six degrees of freedom after having inserted Tibial Stem 400 in the proximal cavity of the tibia.

In addition, it should be understood that the manifestation of the joint linking Tibial Plate 300 and Tibial Stem 400 could be different than the examples herein explained and detailed.

Reference will now be made to an example prosthesis implantation method according to the present invention (of course, this example is intended to be illustrative and not restrictive). More particularly, the example implantation method may comprise:

Providing a multi-part tibial component, where said tibial component includes a tibial plate, a tibial stem, and a locking component. A protuberance may extend from the inferior surface of the tibial plate and the protuberance may be designed to fit with a tibial stem socket.

Preparing the proximal end of a tibia, including at least creating a cavity roughly along the intramedullary canal of the tibia.

Positioning the tibial stem in the prepared cavity. In one example, the socket may be open distally and form a passageway along the tibial stem. In this case, the tibial stem could be placed in the cavity along an intramedullary guide, which mimics the orientation of the natural intramedullary canal.

As an option, the surgeon could use a special cutting tool for which the tip could fit essentially perfectly inside the socket of the tibial stem. The purpose of this cutting tool would be to create a resected surface of the proximal tibia essentially perfectly perpendicular to the socket's axis of revolution.

Positioning the tibial plate relative to the tibial stem. By using the available degrees of freedom (e.g., from 1 to 6), the surgeon can obtain coverage of the resected tibia that is parallel with the inferior surface of the tibial plate relative to the resected surface of the tibia (while the tibial stem maintains the location of the anatomical intramedullary and generally avoids impingement with the cortical bone of the tibia).

As an option, the surgeon can cement the tibial plate to the tibia. In this case, the surgeon removes the tibial plate from the resected tibia and applies the bone cement. Immediately afterwards, the surgeon can reinsert the tibial plate and impact it against the resected tibia. Typically, the curing time of the PMMA bone cement is about 10 minutes. The surgeon could use a compressive screw (not shown in the drawings), which would apply a compressive load between the tibial plate and the resected tibia during the curing stage for the PMMA bone cement (in addition, or in the alternative, one or more compression instruments may be utilized). The screw could be defined by at least two portions: a shoulder head, which would enter through the superior surface of the tibial plate, and a threaded portion compatible with the threaded portion of the tibial stem. With the tibial stem well anchored in the proximal tibia, screwing the compressive screw would apply a load to the superior surface of the tibial plate, and, as a result, pressurize the cement mantle between the inferior surface of the tibial plate and the resected tibia during the curing stage (which would improve (a) the stability of the tibial plate and (b) the penetration of the bone cement into the asperities of the inferior surface and into the tibia). At the end of the curing stage of the PMMA bone cement, the surgeon could remove the compressive screw.

Positioning the locking component, and locking the orientation of the tibial plate relative to the tibial stem.

Finally, locking the tibio-femoral insert on the tibial plate.

As described above, a prosthetic implant suitable for use in connection with knee surgery is provided. Of course (as also mentioned above), the present invention contemplates a prosthetic implant for use in other areas of the body. This is made clear by the following description, which discusses in more general terms a prosthetic implant according to various embodiments of the present invention.

More particularly, the present invention may provide a prosthetic implant, comprising: a plate (e.g., for carrying an articular insert); a stem; and a locking component to lock the plate relative to the stem in a desired orientation (the stem may first be placed in a cavity in an appropriate bone and the plate may then be placed after the stem).

In one example (which example is intended to be illustrative and not restrictive), the plate may be oriented independently of the orientation of the stem before being locked relative thereto by adjustment around at least one degree of freedom.

In another example (which example is intended to be illustrative and not restrictive), the plate may be oriented independently of the orientation of the stem before being locked relative thereto by adjustment around at least two degrees of freedom.

In another example (which example is intended to be illustrative and not restrictive), the plate may be oriented independently of the orientation of the stem before being locked relative thereto by adjustment around at least three degrees of freedom.

In another example (which example is intended to be illustrative and not restrictive), the plate may be oriented independently of the orientation of the stem before being locked relative thereto by adjustment around at least four degrees of freedom.

In another example (which example is intended to be illustrative and not restrictive), the plate may be oriented independently of the orientation of the stem before being locked relative thereto by adjustment around at least five degrees of freedom.

In another example (which example is intended to be illustrative and not restrictive), the plate may be oriented independently of the orientation of the stem before being locked relative thereto by adjustment around six degrees of freedom.

In another embodiment the present invention may provide a prosthetic implant, comprising: a plate (e.g., for carrying an articular insert); a stem; and a locking component to lock the plate relative to the stem in a desired orientation.

In one example (which example is intended to be illustrative and not restrictive), the stem may be first placed and then mated with a stem attachment protuberance that extends from the inferior surface of the plate.

In another example (which example is intended to be illustrative and not restrictive), the overall length of the protuberance calculated perpendicularly to the inferior surface of the plate may be less than about 25 mm.

In another example (which example is intended to be illustrative and not restrictive), the external shape of the stem may define a first axis of revolution (or neutral axis), and the internal cavity of the stem may define a second axis of revolution (or neutral axis).

In another example (which example is intended to be illustrative and not restrictive), the first axis may be collinear with the second axis.

In another example (which example is intended to be illustrative and not restrictive), the first axis may be parallel but not collinear with said second axis (the first axis may be offset from the second axis by a distance between about 1 mm and about 10 mm, for example; in a more specific example, the first axis may be offset from the second axis by a distance of about 5 mm).

In another example (which example is intended to be illustrative and not restrictive), the first axis may be non-parallel with the second axis (the first axis may be angulated from the second axis by an angle of between about 1° and about 10°, for example; in a more specific example, the first axis may be angulated from the second axis by an angle of about 5°).

In another example (which example is intended to be illustrative and not restrictive), a mechanism (e.g., a screw) may be positioned in order to translate inferiorly the plate relative to the anchored stem for the purpose of pressurizing the cement mantle between the surface of the plate and the a bone.

In another example (which example is intended to be illustrative and not restrictive), a method of implanting a prosthesis may comprise the following steps: (a) provide a multi-piece component, the multi-piece component including a plate (e.g., for carrying an articular insert), a stem and a locking component; (b) preparing the proximal end of a bone (e.g., including creating a cavity along an intramedullary canal of the bone); (c) positioning the stem in the prepared cavity; (d) providing a fixation mechanism between the cavity and the stem; (e) optimizing the orientation of the plate relative to the bone (e.g., based upon a desire of a surgeon); (f) when the desired orientation is obtained, impacting the plate against the resected bone; and (g) positioning the locking component to lock the orientation of the plate relative to the stem.

In another example (which example is intended to be illustrative and not restrictive), the surgeon can cement the plate onto the bone. In this regard, immediately after application of the bone cement, the surgeon may insert the plate and compress it against the resected bone. A compressive device inserted between the plate and the fixed stem may be used to apply a load between the plate and the resected bone during the curing stage of the PMMA bone cement and, as a result, pressurize the cement mantle between the surface of the plate and the resected bone during the curing stage.

In another example (which example is intended to be illustrative and not restrictive), the cavity of the stem may be open distally and may form a passageway all along the stem. The stem may thus be placed in the cavity along an intramedullary guide, which mimics the orientation of the natural intramedullary canal.

In another example (which example is intended to be illustrative and not restrictive), the cavity of the stem could be used as a guide to resect the proximal bone.

In another example (which example is intended to be illustrative and not restrictive), a method of implanting a prosthesis for the reimplantation of any joint may comprise the following steps: (a) providing a multi-piece component, the component including a plate (e.g., for carrying an articular insert); a stem and a locking component; (b) preparing the extremity of a bone including at least creating a cavity; (c) positioning the stem in the prepared cavity and fixing the stem to the bone; (d) optimizing the orientation of the plate relative to the bone (e.g., based upon a desire of a surgeon); (e) impacting the plate against the resected bone (once the desired orientation obtained); (f) positioning the locking component to lock the orientation of the plate relative to the stem.

In another example (which example is intended to be illustrative and not restrictive), the surgeon can cement the plate to the bone. In this regard, immediately after application of the bone cement, the surgeon can insert the plate and compress it against the resected bone in cooperation with a feature which will apply a load against the plate and the resected bone during the curing stage of the PMMA bone cement (and as a result pressurize the cement mantle between the surface of the plate and the resected bone during the curing stage).

In another example (which example is intended to be illustrative and not restrictive), the cavity of the stem may be open distally and may form a passageway all along the stem. In this specific case, the stem could be placed in the cavity along an intramedullary guide, which mimics the orientation of the natural intramedullary canal.

In another example (which example is intended to be illustrative and not restrictive), the cavity of the stem may be used as a guide to resect the extremity of a bone.

Figure 6:
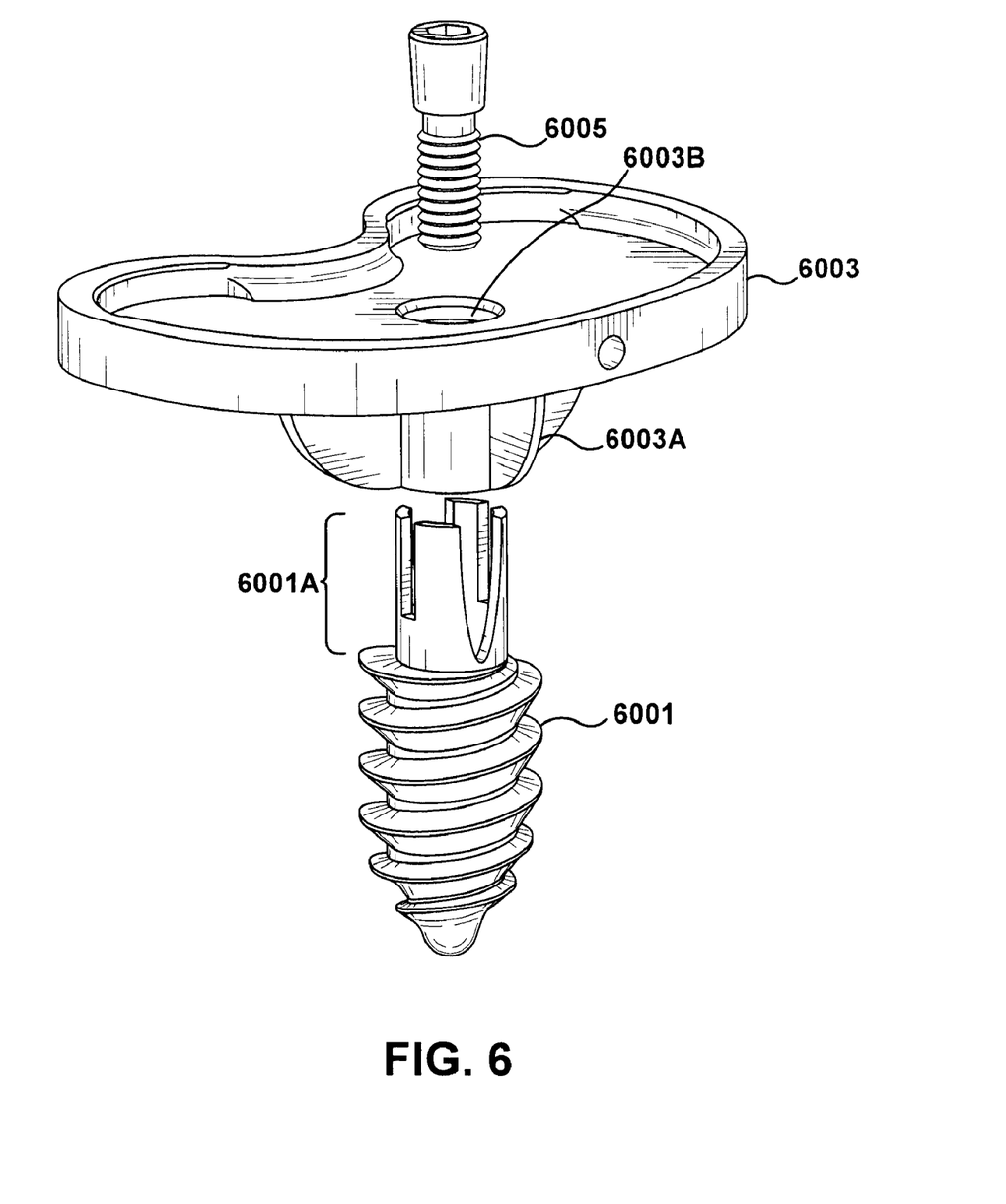
FIG. 6 shows a partially exploded perspective view of an apparatus according to another embodiment of the present invention.

Referring now to FIG. 6, a partially exploded perspective view of an apparatus according to another embodiment of the present invention is shown. As seen in this Fig., Tibial Stem 6001 may be anchored in a cavity created in the proximal tibia (in one example, Tibial Stem 6001 may be in the form of a self-tap screw). Further, Tibial Plate 6003 may be affixed to Tibial Stem 6001 via Locking Component 6005. Of note, Tibial Stem 6001 may include internal threads (not shown) and Shaft Portion 6001A, which may have vertical slots therein. Further, Tibial Plate 6003 may include Protuberance 6003A. Further still, Protuberance 6003A may include Internal Passage 6003B (e.g., axially aligned with the hole in Tibial Plate 6003) for receiving therein Shaft Portion 6001A. The outside of at least a portion of Locking Component 6005 and/or at least a portion of the inside of the passage in Shaft Portion 6001A may be tapered such that as Locking Component 6005 is threaded down into Tibial Stem 6001 (through the hole in Tibial Stem 6001) the outside of Shaft Portion 6001A expands (via the outward force generated by the above-mentioned tapered elements and aided by the presence of the vertical slots) against the inside of the Internal Passage 6003B of Protuberance 6003A. This expansion thus locks the orientation of the Tibial Plate 6003 relative to the anchored Tibial Stem 6001.

Figure 7A:
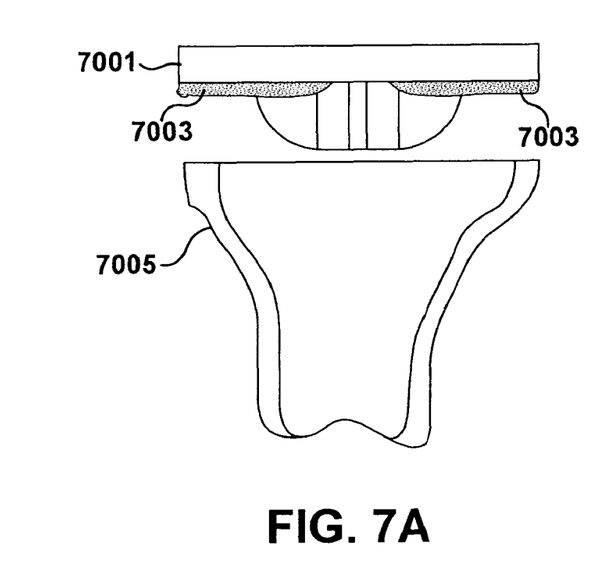
FIGS. 7A and 7B show how an embodiment of the present invention improves the implant-bone fixation by pressurizing the cement mantle during the curing stage.
Figure 7B:
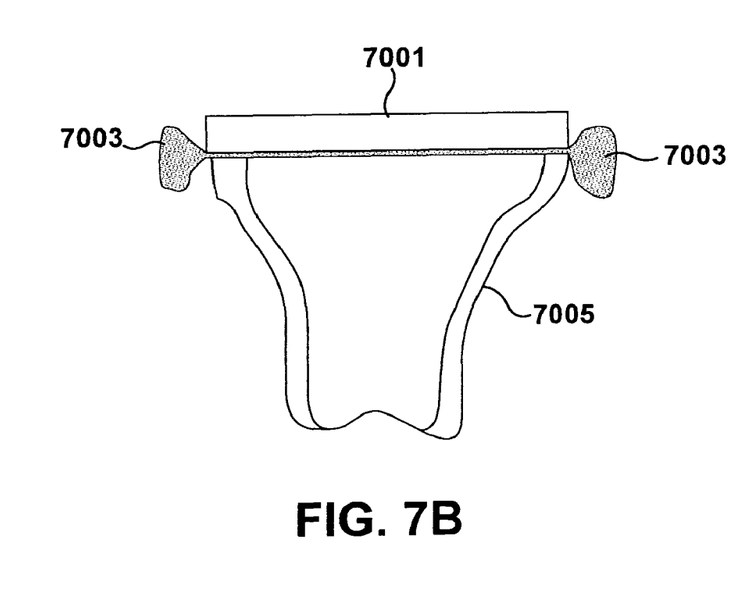

Referring now to FIGS. 7A and 7B, it is seen how in one embodiment Tibial Plate 7001 pressurizes Cement 7003 against the proximal Tibia 7005 during the curing stage.

Figure 8:
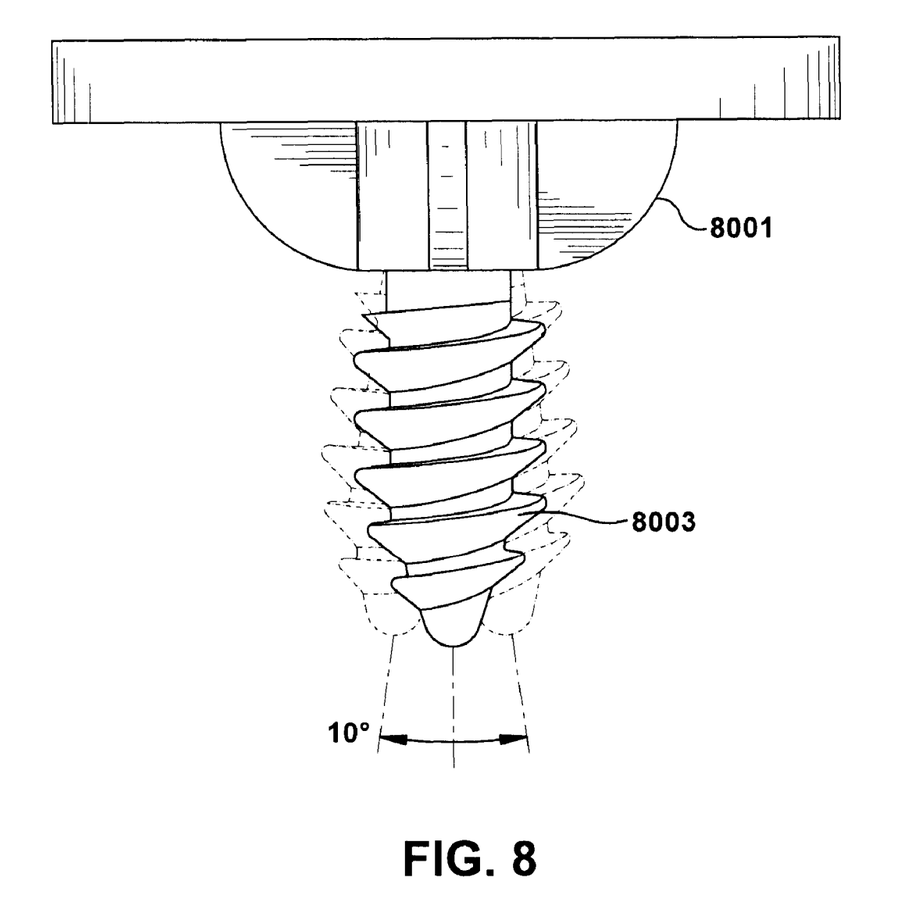
FIG. 8 shows how an embodiment of the present invention allows an angular mismatch between the plate (e.g., tibial plate) and the stem (e.g., in the form of a self-tap screw)

Referring now to FIG. 8, it is seen how an embodiment of the present invention allows an angular mismatch between the Plate 8001 (e.g., tibial plate) and Stem 8003 (e.g., in the form of a self-tap screw). Of note, 10 degrees is given as an example only.

Figure 9:
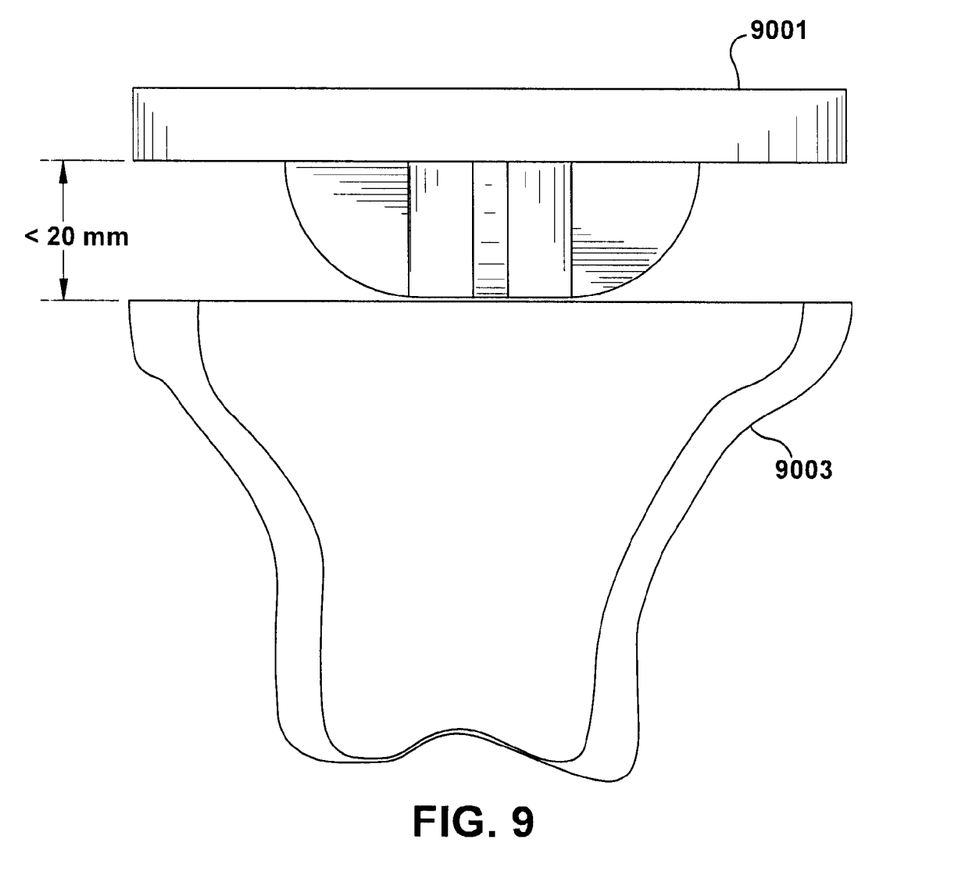
FIG. 9 shows how an embodiment of the present invention permits implantation of the plate (e.g., tibial plate) through a relatively small exposure (e.g., via minimally invasive surgery).

Referring now to FIG. 9, it is seen how an embodiment of the present invention permits implantation (e.g., using one or more instruments) of Plate 9001 (e.g., tibial plate) adjacent Bone 9003 (e.g., a proximal tibia) through a relatively small exposure (e.g., via minimally invasive surgery). Of note, <20 mm is given as an example only (in one specific example, the overall height including the protuberance may be <20 mm, in another specific example, the height of the protuberance itself may be <20 mm).

In another embodiment, a porous coated plate may be held rigidly against the bone, i.e., a non-cemented application (initial rigid fixation may be critical to promoting bony ingrowth. Thus, various embodiments of the present invention may utilize an in growth plate in order to increase the success rate (as compared, for example, to conventional non-modular designs).

In another embodiment, a prosthesis for attachment to a bone of a patient is provided, comprising: a stem anchored in a cavity in the bone; a plate placed adjacent the anchored stem; and a locking component that affixes the plate to the anchored stem, wherein the locking component is inserted through a hole in the plate into the anchored stem in order to affix the plate to the anchored stem.

In one example, the stem may have external threads and the stem may be anchored in the cavity by being screwed into the cavity.

In another example, the stem may be anchored in the cavity by being impacted into the bone.

In another example, the stem may have at least one external geometrical feature to anchor the stem in the cavity.

In another example, the external geometrical feature may comprise at least one groove.

In another example, a desired orientation of the plate relative to the anchored stem may be independent of the orientation of the anchored stem.

In another example, the locking component may affix the plate to the anchored stem in the desired orientation.

In another example, the plate may be cemented against the bone.

In another example, a compressive load may be applied between the anchored stem and the plate to pressurize a cement mantle between the bone and the plate while the cement cures.

In another example, the compressive load may be applied by an instrument, wherein the instrument provides translation of the plate relative to the anchored stem and toward the anchored stem to pressurize the cement mantle.

In another example, the locking component may comprise a threaded fastener.

In another example, the locking component may have external threads, wherein the stem may have internal threads and wherein the locking component may affix the plate to the anchored stem via mating of the external threads of the locking component with the internal threads of the anchored stem.

In another example, the stem may comprise a socket for receiving therein a protuberance extending from the plate.

In another example, an internal passage in the protuberance may taper from larger to smaller in a direction moving away from the plate, such that insertion of the locking component through the hole in the plate and into the protuberance may cause the protuberance to expand radially against an inner surface of the socket of the anchored stem to lock the orientation of the plate relative to the anchored stem.

In another example, the protuberance may have an internal passage and wherein the locking component may have at least one portion that tapers from larger to smaller in a direction moving from a proximal end to a distal end, such that insertion of the locking component through the hole in the plate and into the protuberance may cause the protuberance to expand radially against an inner surface of the socket of the anchored stem to lock the orientation of the plate relative to the anchored stem.

In another example, an internal passage in the protuberance may taper from larger to smaller in a direction moving away from the plate and wherein the locking component may have at least one portion that tapers from larger to smaller in a direction moving from a proximal end to a distal end, such that insertion of the locking component through the hole in the plate and into the protuberance may cause the protuberance to expand radially against an inner surface of the socket of the anchored stem to lock the orientation of the plate relative to the anchored stem.

In another example, the plate may comprise a protuberance extending therefrom, wherein the protuberance may comprise an internal passage therein, and wherein a shaft of the stem may be received into the internal passage of the protuberance.

In another example, the locking component may have at least one portion that tapers from larger to smaller in a direction moving from a proximal end to a distal end, such that insertion of the locking component through the hole in the plate and into an internal passage of the shaft of the stem may cause the shaft of the stem to expand radially against the internal passage of the protuberance to lock the orientation of the plate relative to the anchored stem.

In another example, an internal passage of the shaft of the stem may have at least one portion that tapers from larger to smaller in a direction moving from a proximal end to a distal end, such that insertion of the locking component through the hole in the plate and into the internal passage of the shaft of the stem may cause the shaft of the stem to expand radially against the internal passage of the protuberance to lock the orientation of the plate relative to the anchored stem.

In another example, all internal passage of the shaft of the stem may have at least one portion that tapers from larger to smaller in a direction moving from a proximal end to a distal end and wherein the locking component may have at least one portion that tapers from larger to smaller in a direction moving from a proximal end to a distal end, such that insertion of the locking component through the hole in the plate and into the internal passage of the shaft of the stem may cause the shaft of the stem to expand radially against the internal passage of the protuberance to lock the orientation of the plate relative to the anchored stem.

In another example, the bone may be a tibia and the plate may be placed over the anchored stem.

In another example, the cavity may run generally along an intramedullary canal of the tibia.

In another example, a femoral bearing insert may be placed on a superior surface of the plate.

In another example, the bone may be a femur and the plate may be placed under the anchored stem.

In another example, the cavity may run generally along an intramedullary canal of the femur.

In another example, a femoral bearing insert may be placed on an inferior surface of the plate.

In another embodiment, a method of attaching a prosthesis to a bone of a patient is provided, comprising: creating a cavity in the bone; anchoring a stem in the cavity; placing a plate adjacent the anchored stem; and affixing the plate to the anchored stem by inserting a locking component through a hole in the plate into the anchored stem.

In one example, the method may further comprise placing cement on the bone.

In another example, the method may further comprise pressurizing a cement mantle by translation of the plate generally perpendicular to the resected bone relative to the anchored stem.

In another example, the stem may have external threads and the stem may be anchored in the cavity by being screwed into the cavity.

In another example, the stem may be anchored in the cavity by being impacted into the bone.

In another example, the stem may have at least one external geometrical feature to anchor the stem in the cavity.

In another example, the external geometrical feature may comprise at least one groove.

In another example, a desired orientation of the plate relative to the anchored stem may be independent of the orientation of the anchored stem In another example, the locking component may affix the plate to the anchored stem in the desired orientation.

In another example, the method may further comprise pressurizing the cement mantle between the bone and the plate while the cement cures.

In another example, the bone may be a tibia and the plate may be placed over the anchored stem.

In another example, the cavity may run generally along an intramedullary canal of the tibia.

In another example, a femoral bearing insert may be placed on a superior surface of the plate.

In another example, the bone may be a femur and the plate may be placed under the anchored stem.

In another example, the cavity may run generally along an intramedullary canal of the femur.

In another example, a, femoral bearing insert may be placed on an inferior surface of the plate.

In another example, the prosthesis may be implanted via minimally invasive surgery.

In another embodiment, a method of attaching a prosthesis to a bone of a patient is provided, comprising: creating a cavity in the bone; anchoring a stem in the cavity; placing a plate adjacent the anchored stem; and affixing the plate to the anchored stem in a desired orientation relative to the anchored stem after placing the plate adjacent the anchored stem.

In one example, the method may further comprise placing cement on the bone.

In another example, the method may further comprise pressurizing a cement mantle by translation of the plate generally perpendicular to the resected bone relative to the anchored stem.

In another example, the stem may have external threads and the stem may be anchored in the cavity by being screwed into the cavity.

In another example, the stem may be anchored in the cavity by being impacted into the bone.

In another example, the stem may have at least one external geometrical feature to anchor the stem in the cavity.

In another example, the external geometrical feature may comprise at least one groove.

In another example, a desired orientation of the plate relative to the anchored stem may be independent of the orientation of the anchored stem.

In another example, the locking component may affix the plate to the anchored stem in the desired orientation.

In another example, the locking component may affix the plate to the anchored stem in the desired orientation by being inserted through a hole in the plate into the anchored stem.

In another example, the method may further comprise pressurizing the cement mantle between the bone and the plate while the cement cures.

In another example, the bone may be a tibia and the plate may be placed over the anchored stem.

In another example, the cavity may run generally along an intramedullary canal of the tibia.

In another example, a femoral bearing insert may be placed on a superior surface of the plate.

In another example, the bone may be a femur and the plate may be placed under the anchored stem.

In another example, the cavity may run generally along an intramedullary canal of the femur.

In another example, a femoral bearing insert may be placed on an inferior surface of the plate.

In another example, the prosthesis may be implanted via minimally invasive surgery.

In another example, a surface of the plate adjacent the bone may have a porous coating and no cement is applied between the bone and the plate.

While a number of embodiments of the present invention have been described, it is understood that these embodiments are illustrative only, and not restrictive, and that many modifications may become apparent to those of ordinary skill in the art. For example, any element described herein may be provided in any desired size (e.g., any element described herein may be provided in any desired custom size or any element described herein may be provided in any desired size selected from a "family" of sizes, such as small, medium, large). Further, one or more of the components may be made from any of the following materials: (a) any biocompatible material (which biocompatible material may be treated to permit surface bone in growth or prohibit surface bone in growth—depending upon the desire of the surgeon); (b) a plastic; (c) a fiber; (d) a polymer; (e) a metal (a pure metal such as titanium and/or an alloy such as Ti—Al—Nb, Ti-6Al-4V, stainless steel); (f) any combination thereof. Further still, any number of female features that increase the cement mantle may be utilized with a given prosthesis. Further still, any number of male features that could dig into the bone so that initial/supplemental fixation can be improved may be utilized with a given prosthesis. Further still, any number of bone screws (e.g., such as for initial fixation and/or such as for supplemental fixation) may be utilized with a given prosthesis. Further still, the plate described herein may be of any desired shape and may comprise, for example, a tibial plate, a femoral plate and/or any other desired prosthetic element. Further still, the stem described herein may be of any desired shape and may comprise, for example, a tibial stem, a femoral stem and/or any other desired prosthetic element. Further still, any steps described herein may be carried out in any desired order (and any additional steps may be added as desired and any steps may be deleted as desired).

What is claimed is:

1. A tibial prosthesis for attachment to a tibial bone of a patient, comprising:
    a tibial stem adapted to be anchored in a cavity in the tibial bone, wherein the tibial stem comprises a socket;
    a tibial plate comprising a superior surface and an inferior surface, wherein a protuberance sized to fit inside the tibial stem socket extends from the inferior surface of the tibial plate, and wherein the tibial plate and the protuberance define a through-channel axially extending all the way through the superior surface, the inferior surface and the protuberance; and
    a locking component having a threaded portion, and a head, wherein the locking component is adapted to be inserted through the through-channel in the tibial plate, wherein an internal passage in the protuberance tapers from larger to smaller in a direction moving away from the superior surface of the tibial plate, such that insertion of the locking component through the through-channel in the tibial plate and into the protuberance causes the protuberance to expand radially against an inner surface of the socket of the tibial stem to lock the orientation of the tibial plate relative to the tibial stem.

2. The tibial prosthesis of claim 1, wherein the tibial stem has external threads and the tibial stem is anchored in the cavity by being screwed into the cavity.

3. The tibial prosthesis of claim 1, wherein the tibial stem is anchored in the cavity by being impacted into the tibial bone.

4. The tibial prosthesis of claim 1, wherein the tibial stem has at least one external geometrical feature to anchor the tibial stem in the cavity.

5. The tibial prosthesis of claim 4, wherein the external geometrical feature comprises at least one groove.

6. The tibial prosthesis of claim 1, wherein, when the tibial stem is anchored in the cavity of the tibial bone, a desired orientation of the tibial plate relative to the anchored tibial stem is independent of the orientation of the anchored tibial stem.

7. The tibial prosthesis of claim 6, wherein the locking component affixes the tibial plate to the anchored tibial stem in the desired orientation.

8. The tibial prosthesis of claim 1, wherein the tibial plate is cemented against the tibial bone.

9. The tibial prosthesis of claim 1, wherein the head of the locking component is tapered from larger to smaller in a direction moving from a proximal end to a distal end.

10. A tibial prosthesis for attachment to a tibial bone of a patient, comprising:
    a tibial stem adapted to be anchored in a cavity in the tibial bone, wherein the tibial stem comprises a socket;
    a tibial plate comprising a superior surface and an inferior surface, wherein a protuberance sized to fit inside the tibial stem socket extends from the inferior surface of the tibial plate, and wherein the tibial plate and the protuberance define a through-channel axially extending all the way through the superior surface, the inferior surface and the protuberance; and
    a locking component having a threaded portion, and a tapered portion that tapers from larger to smaller in a direction moving from a proximal end to a distal end, wherein the locking component is adapted to be inserted through the through-channel in the tibial plate,
wherein an internal passage in the protuberance tapers from larger to smaller in a direction moving away from the superior surface of the tibial plate, such that insertion of the locking component through the through-channel in the tibial plate and into the protuberance causes the protuberance to expand radially against an inner surface of the socket of the tibial stem to lock the orientation of the tibial plate relative to the tibial stem.

11. The tibial prosthesis of claim 10, wherein the tibial stem has external threads and the tibial stem is anchored in the cavity by being screwed into the cavity.

12. The tibial prosthesis of claim 10, wherein the tibial stem is anchored in the cavity by being impacted into the tibial bone.

13. The tibial prosthesis of claim 10, wherein the tibial stem has at least one external geometrical feature to anchor the tibial stem in the cavity.

14. The tibial prosthesis of claim 13, wherein the external geometrical feature comprises at least one groove.

15. The tibial prosthesis of claim 10, wherein, when the tibial stem is anchored in the cavity of the tibial bone, a desired orientation of the tibial plate relative to the anchored tibial stem is independent of the orientation of the anchored tibial stem.

16. The tibial prosthesis of claim 15, wherein the locking component affixes the tibial plate to the anchored tibial stem in the desired orientation.

17. The tibial prosthesis of claim 10, wherein the tibial plate is cemented against the tibial bone.

18. A tibial prosthesis for attachment to a tibial bone of a patient, comprising:
    a tibial stem adapted to be anchored in a cavity in the tibial bone, wherein the tibial stem comprises an internally threaded socket;
    a tibial plate comprising a superior surface and an inferior surface, wherein a protuberance sized to fit inside the tibial stem socket extends from the inferior surface of the tibial plate, and wherein the tibial plate and the protuberance define a through-channel axially extending all the way through the superior surface, the inferior surface and the protuberance; and
    a locking component having a threaded portion intended to be received by the threaded socket of the tibial stem, and a head, wherein the locking component is adapted to be inserted through the through-channel in the tibial plate, wherein an internal passage in the protuberance tapers from larger to smaller in a direction moving away from the superior surface of the tibial plate, such that insertion of the locking component through the through-channel in the tibial plate and into the protuberance causes the protuberance to expand radially against an inner surface of the socket of the tibial stem to lock the orientation of the tibial plate relative to the tibial stem.

19. The tibial prosthesis of claim 18, wherein the tibial stem has external threads and the tibial stem is anchored in the cavity by being screwed into the cavity.

20. The tibial prosthesis of claim 18, wherein the tibial stem is anchored in the cavity by being impacted into the tibial bone.

21. The tibial prosthesis of claim 18, wherein the tibial stem has at least one external geometrical feature to anchor the tibial stem in the cavity.

22. The tibial prosthesis of claim 21, wherein the external geometrical feature comprises at least one groove.

23. The tibial prosthesis of claim 18, wherein, when the tibial stem is anchored in the cavity of the tibial bone, a desired orientation of the tibial plate relative to the anchored tibial stem is independent of the orientation of the anchored tibial stem.

24. The tibial prosthesis of claim 23, wherein the locking component affixes the tibial plate to the anchored tibial stem in the desired orientation.

25. The tibial prosthesis of claim 18, wherein the tibial plate is cemented against the tibial bone.

26. The tibial prosthesis of claim 18, wherein the head of the locking component is tapered from larger to smaller in a direction moving from a proximal end to a distal end.

\* \* \* \* \*